US008435532B2

(12) United States Patent
Nilsson

(10) Patent No.: US 8,435,532 B2
(45) Date of Patent: May 7, 2013

(54) USE OF MODIFIED EXTRACELLULAR MATRIX PROTEINS IN DIAGNOSIS AND TREATMENT OF ATHEROSCLEROSIS

(75) Inventor: Jan Nilsson, Genarp (SE)

(73) Assignee: CardioVax, LLC, Torrance, CA (US)

( * ) Notice: Subject to any disclaimer, the term of this patent is extended or adjusted under 35 U.S.C. 154(b) by 0 days.

(21) Appl. No.: 13/569,051

(22) Filed: Aug. 7, 2012

(65) Prior Publication Data

US 2012/0301491 A1 Nov. 29, 2012

Related U.S. Application Data

(63) Continuation of application No. 12/814,137, filed on Jun. 11, 2010, now abandoned, which is a continuation of application No. 11/523,366, filed on Sep. 19, 2006, now abandoned, which is a continuation of application No. PCT/SE2005/000394, filed on Mar. 17, 2005.

(30) Foreign Application Priority Data

Mar. 19, 2004 (SE) ........................................ 0400683

(51) Int. Cl.
*A61K 39/00* (2006.01)
(52) U.S. Cl.
USPC .................................... 424/184.1; 424/185.1
(58) Field of Classification Search ........................ None
See application file for complete search history.

(56) References Cited

FOREIGN PATENT DOCUMENTS

WO 97/23783 7/1997
WO 02/080954 10/2002

OTHER PUBLICATIONS

Pontus Duner. Immune Responses Against Aldehyde Modified Extracellular Matrix in Atherosclerosis. Dissertation, Oct. 2009. pp. 1-53.*

Menzel et al. "Effects of aminoguanidine on adhesion molecule expression of human endothelial cells." Pharmacology 55:126-135, 1997.
Yamamoto et al. "Possible involvement of increased glycoxidation and lipid peroxidation of elastin in atherogenesis in haemodialysis patients," Nephrol. Dial. Transpant. 17:630-636, 2002.
Lee et al. "Collagen-linked fluorescence in human atherosclerotic plaques," Atherosclerosis 98:219-227, 1993.
Hill et al. "Associaation of malondialdehyde-acetaldehyde (MMA) adducted proteins with atherosclerotic-induced vascular inflammatory injury," Atherosclerosis 141:107-116, 1998.
Slatter et al. "The importance of lipid-derived malondialdehyde in diabetes mellitus," Diabetologia 43:550-557, 2000.
International Search Report from corresponding PCT application PCT/SE2005/000394, 2005.
Plainski et al. "ApoE-deficient mice are a model of lipoprotein oxidation in atherogenesis. Demonstration of oxidation-specific epitopes in leases and high titers of autoantibodies to malondialdehyde-lysine in serum," Arterioscler. Thromb. Vasc. Biol. 14:605-616, 1994.
George et al. "Atherosclerosis in LDL-receptor knock-out mice is accelerated by immunization with anti-cardiolipin antibodies," Lupus 6:723-729, 1997.
Afek et al. "Enhancement of atherosclerosis in beta-2-glycoprotein I-immunized apolipoprotein E-deficient mice," Pathobiology 67:19-25, 1999.
Duner et al. "Immune responses against fibronectin modified by lipoprotein oxidation and their association with cardiovascular disease," J. Int. Med. 265:593-603, 2009.
Duner et al. "Immunization of apoE-/- mice with aldehyde-modified fibronectin inhibits the development of atherosclerosis," Cardiovasc. Res. 91:528-36, 2011.
Sengoelge et al. "Endothelial cell adhesion molecule and PMNL response to inflammatory stimuli and AGE-modified fibronectin," Kidney Int. 54:1637-51, 1998.

* cited by examiner

*Primary Examiner* — Maher Haddad
(74) *Attorney, Agent, or Firm* — K&L Gates LLP; Louis C. Cullman; Michelle Glasky Bergman

(57) ABSTRACT

The present invention relates to the use of fibronectin, tenascin, collagens type I, III, VI and/or VIII modified by aldehyde or by glycosylation in ELISA for detection of antibodies in plasma and serum to diagnose atherosclerosis as well as the use of induction of tolerance and active as well as passive immunization against glycosylated or aldehydemodified fibronectin, tenascin, collagen type I, III, VI and/or VIII for prevention and treatment of atherosclerosis.

1 Claim, 4 Drawing Sheets

USE OF MODIFIED EXTRACELLULAR MATRIX PROTEINS IN DIAGNOSIS AND TREATMENT OF ATHEROSCLEROSIS

PRIORITY INFORMATION

This application is a continuation of U.S. patent application Ser. No. 12/814,137 filed Jun. 11, 2010, now abandoned which is a continuation of U.S. patent application Ser. No. 11/523,366 filed Sep. 19, 2006, now abandoned which is a continuation of PCT application PCT/SE2005/000394, filed on Mar. 17, 2005, which claims priority to Swedish application 0400683-9, filed on Mar. 19, 2004, all of which are incorporated herein by reference in their entireties.

TECHNICAL FIELD

The present invention relates to the use of certain connective tissue proteins or derivatives thereof for detection of antibodies in plasma and serum to diagnose atherosclerosis, as well as the use of antibodies against such connective tissue proteins or derivatives thereof produced by immunization or recombinant technique for detection of certain connective tissue proteins or derivatives thereof in plasma and serum to diagnose presence of unstable and rupture-prone atherosclerotic plaques.

BACKGROUND OF THE INVENTION

Atherosclerosis is a degenerative disease of medium- and large-sized arteries. It is the major cause of acute myocardial infarction, stroke and peripheral artery disease. The first stages of the disease are characterized by accumulation of cholesterol-loaded macrophages forming small fatty streaks on the inside of the arterial wall. Activation of a chronic inflammatory process within these fatty streaks leads to the formation of raised fibromuscular plaques with various degree of extracellular lipid and cell necrosis. In plaques with extensive cell death and inflammation the fibrous cap covering the core of lipid deposits becomes eroded increasing the risk for plaque rupture and thrombotic occlusion of the vessel, i.e. the major cause of acute clinical events.

The disease is initiated by accumulation of lipoproteins, primarily LDL, in the extracellular matrix of the arterial intima. This accumulation is caused by binding of positively charged amino acids in the LDL protein apo B-100 to negatively charged matrix glycoproteins. The entrapped LDL aggregates and becomes oxidized in response various enzymes and oxygen radicals present in the arterial wall. The oxidation of LDL is associated with formation of a number of highly reactive compounds such as aldehydes, lipid peroxides and oxysterols that will cause neighbouring endothelial cells to express adhesion molecules and activate an inflammatory response. As a result monocytes and T cells will infiltrate the affected intima and the monocytes will differentiate into macrophages expressing different types of scavenger receptors. These receptors effectively bind and mediate the uptake and removal of oxidized LDL from the extracellular matrix. The macrophages will subsequently express oxidized LDL antigens associated with HLA-DR receptors. Recognition of these antigens by specific T cells results in activation of an adaptive immune response against oxidized LDL. The important role of this immune response in the development of atherosclerosis is becoming increasingly recognized.

The oxidation of LDL is also associated with a degradation of apo B-100 into peptide fragments that are further modified by reaction aldehydes such as malondialdehyde (MDA) and 4-hydroxynonenal. These aldehyde-modified peptide fragments become major targets for the immune system and antibodies against MDA-modified apo B-100 fragments are frequently encountered in human plasma. The role of these immune responses remains to be fully characterized but animal experiments demonstrating that immunization with oxidized LDL inhibits the development of atherosclerosis suggest that at least some of these immune responses have a protective effect.

SUMMARY OF THE INVENTION

As discussed above it is generally believed that the oxidation of LDL mainly occurs while LDL is bound to glycosaminoglycans and other extracellular matrix proteins in the arterial wall. However, a possibility that remains largely unexplored is that reactive aldehydes that are generated during LDL oxidation may not only react with apo B-100 but also with the extracellular matrix proteins to which the LDL is adhered. If this happens it is likely to result in fragmentation and aldehyde-modification also of the respective matrix protein.

DETAILED DESCRIPTION OF THE INVENTION

Figure 1:
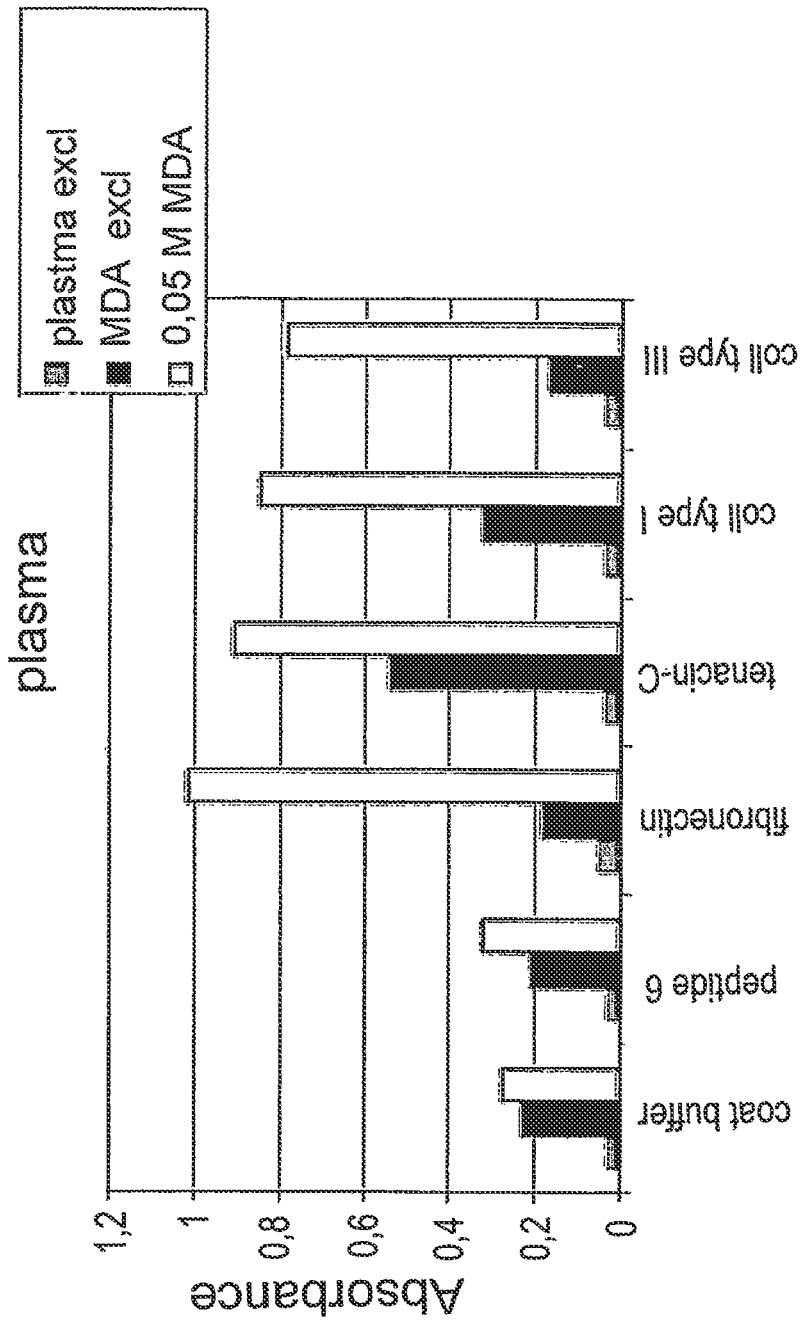
FIGS. 1 and 2 are graphs showing the presence of antibodies against DMA-modified extracellular matrix proteins in normal human plasma.

The present invention in particular relates to the use of fibronectin, tenascin, collagens type I, III, VI and/or VIII modified by aldehyde or by glycosylation in ELISA for detection of antibodies in plasma and serum to diagnose atherosclerosis.

In a preferred embodiment the fibronectin, tenascin, collagens type I, III, VI and VIII have been modified by malondialdehyde.

A further preferred embodiment relates to the use of antibodies against glycosylated or aldehyde-modified fibronectin, tenascin, collagens type I, III, VI and VIII produced by immunization or recombinant technique for detection of aldehyde-modified or glycosylated fibronectin, tenascin, collagen type I, III, VI and/or VIII in plasma and serum to diagnose presence of unstable and rupture-prone atherosclerotic plaques.

A still further preferred embodiment relates to the use of labelled antibodies against glycosylated or aldehyde-modified fibronectin, tenascin, collagens type I, III, VI and/or VIII produced by immunization or recombinant technique in imaging of atherosclerotic plaques.

A further aspect of the invention relates to the use of induction of tolerance and active as well as passive immunization against glycosylated or aldehyde-modified fibronectin, tenascin, collagen type I, III, VI and/or VIII for prevention and treatment of atherosclerosis.

When an aldehyde-modification and fragmentation of extracellular matrix proteins occurs in atherosclerotic plaques it is an important part of the disease process. Like the aldehyde-modified fragments of apo B-100 also aldehyde-modified peptide sequences in extracellular matrix proteins may become targets for autoimmune responses. This will result in recruitment of macrophage releasing matrix-degrading enzymes and erosion of plaque connective tissue and increase the risk for plaque rupture. When so, an aldehyde modification of extracellular matrix proteins is a critical factor in development of plaque rupture and acute cardiovascular events. It also points to the possibility of developing novel therapies for atherosclerosis by manipulating these immune responses through passive or active immunization or by induction of tolerance depending on if the main effect of the immune response is atherogenic or atheroprotective.

The enzymatic degradation of aldehyde-modified matrix proteins is also associated with a release of such degradation products into the circulation. This is of importance because the presence of such proteins in the circulation may act as markers of emerging plaque instability. The availability of a marker for emerging plaque instability would be of considerable value in identifying patients at high risk for development of acute myocardial infarction and stroke. Several effective invasive and non-invasive therapies for unstable plaques have been clinically established, However, the challenge remains to identify subjects with unstable plaques before they suffer an acute event. In subjects suffering from an acute myocardial infarction up to 30% die before reaching the hospital.

Results

To provide initial indirect evidence for the existence of oxidative damages of extracellular matrix proteins in humans presence of immune response against aldehyde-modified extracellular matrix proteins was investigated by analyzing if antibodies against such proteins are present in human plasma.

The vascular extracellular matrix proteins fibronectin, tenascin, biglycan, decorin, collagen type I, III, VI and VIII were coated on the bottom of 96-well microtiter plates. The plates were subsequently washed in 0.05% Tween-20 and incubated with Superblock. Aldehyde-modification was achieved by incubation with 0.05M MDA for 37° C. for 3 hr. After washing in 0.05% Tween-20 the wells were incubated with human plasma (pooled from 50 healthy blood donors), rinsed and incubated with goat anti-human biotinylated IgM. Detection was performed using AP-conjugated streptavidin and NPP substrate.

Figure 2:
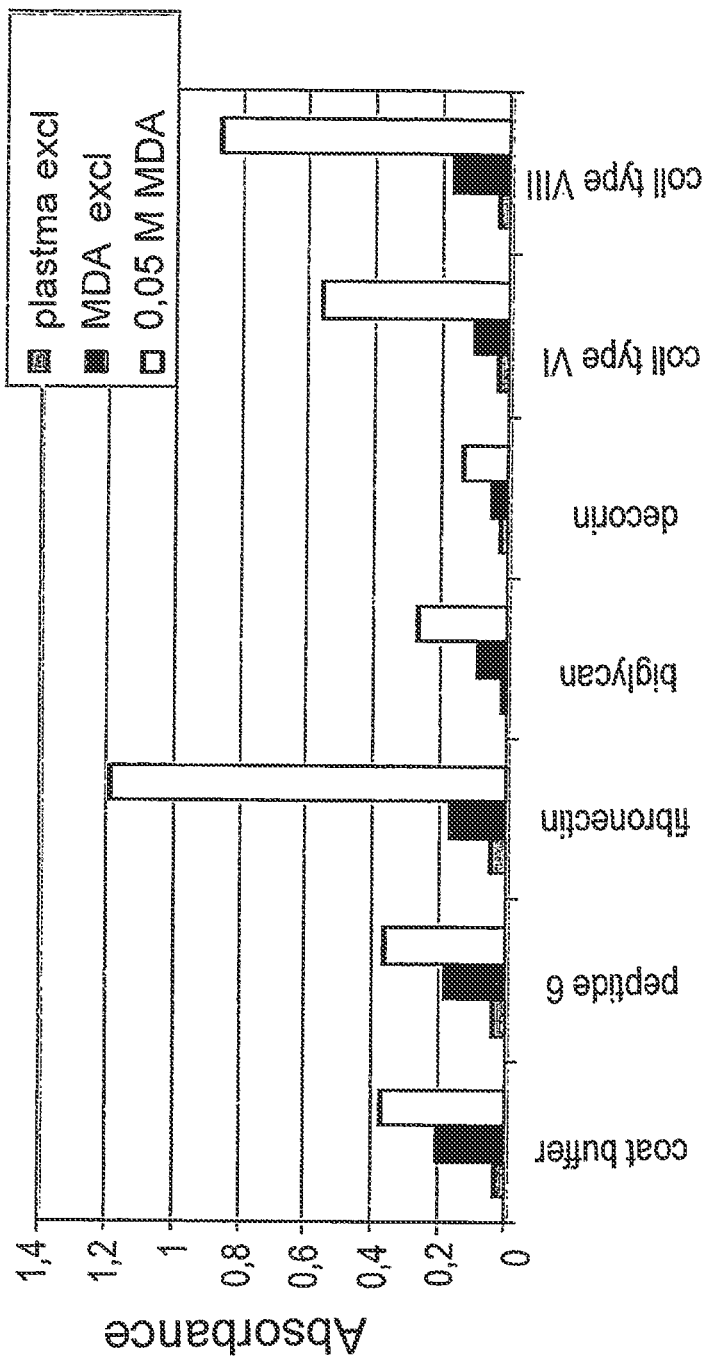

The results obtained in the ELISA analyses demonstrated presence of antibodies against aldehyde-modified fibronectin, tenascin, collagen type I, III, VI and VIII, but not against aldehyde-modified biglycan and decorin in human plasma (FIGS. 1 and 2). These findings demonstrate that immune responses against vascular extracellular matrix proteins exist in humans. Accordingly, they also provide evidence for the existence of oxidative damages of extracellular matrix proteins.

The antibody assay may utilise any tissue and the determinations are made using any immuno-cyto-histochemical method, any immunoassay including, ELISA, Elispot, RIA and others any blotting technique, including Western blotting, Southern blotting and others, any bioassay, any tissue culture technique, RT-PCR, flow cytometry, cytometric bead array, DNA microarray and/or proteomics.

Figure 3:
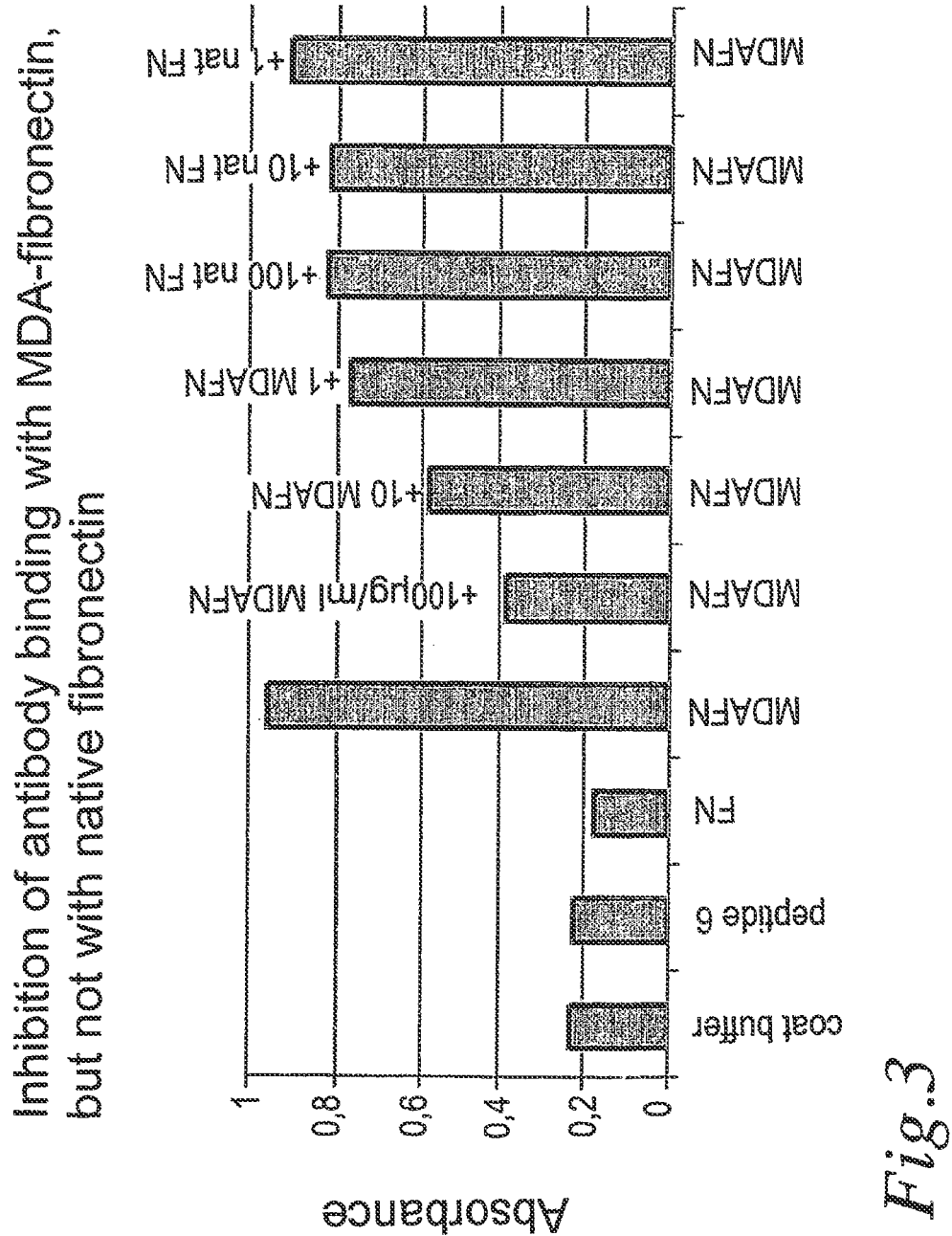
FIG. 3 is a graph showing inhibition of antibody binding with DMA-fibronectin, but not with native fibronectin.

Additional preliminary experiments were done on immune responses against MDA modified fibronectin. It was found that preincubation of human plasma with MDA modified fibronectin inhibited antibody-binding in the ELISA demonstrating the specificity of the assay (FIG. 3).

Figure 4:
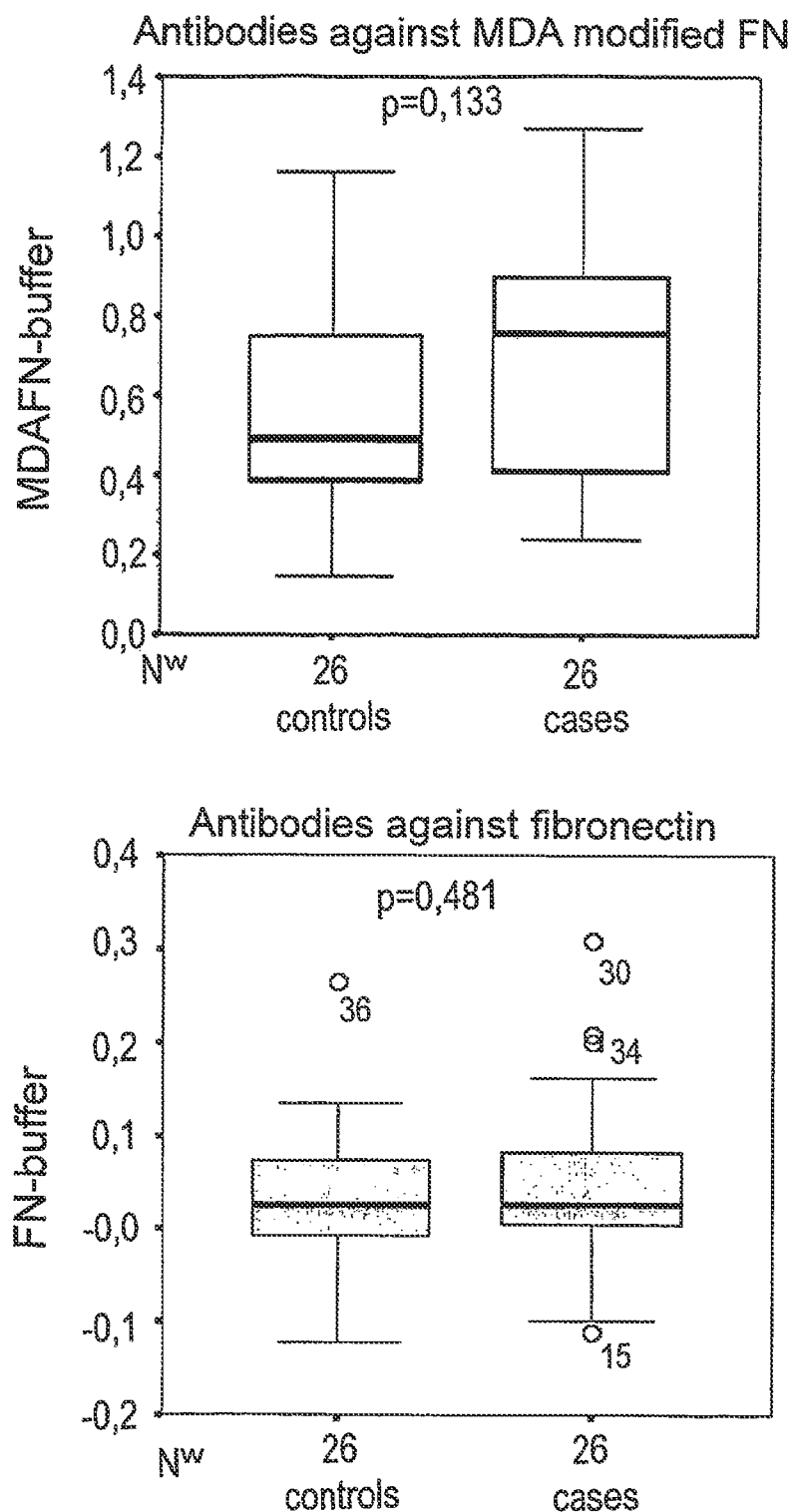
FIG. 4 includes graphs showing antibodies against MDA modified fibronectin and fibronectin.

Finally, a small pilot clinical study was performed to assess the role of immune responses against aldehyde-modified fibronectin in cardiovascular disease. The study group was recruited from the Malmö Diet Cancer Study and consisted of 26 subjects that developed an acute myocardial infraction during a 5-year follow up period and 26 healthy controls matched for age, sex and smoking. The level of antibodies against aldehyde-modified fibronectin was determined in plasma samples obtained at the baseline investigation. Antibodies against aldehyde-modified fibronectin tended to be higher among those that later developed a myocardial infarction whereas the levels of antibodies against native fibronectin were low an equally distributed between the two groups (FIG. 4).

There was also a trend for an association between antibodies against aldehyde-modified fibronectin and carotid artery intima media thickness (an indirect measure of the severity of atherosclerosis) in the study (r=0.20, p=0.11). These observations suggest that immune responses against aldehyde matrix proteins such as fibronectin may be involved in atherosclerosis and serve as markers of disease risk and severity. However, additional studies are required in order to establish this hypothesis.

For the induction of tolerance mucosal immunization is used, whereby an obtained activation of the immuno response or tolerance is dependent on the dose of antigen and has to be tested out, as such.

To provide for an active immunization antigen extracted proteins or synthetic peptide fragments. Theoretically recombinantly produced proteins and protein fragments can be used as well.

At passive immunization one may use either antibodies directed to whole proteins or to peptides.

What is claimed is:

1. A method for decreasing the risk for rupture-prone atherosclerotic plaques in a subject comprising immunizing the subject with an effective amount of malondialdehyde modified fibronectin.

* * * * *